United States Patent [19]

Devadas et al.

[11] Patent Number: 5,338,858
[45] Date of Patent: Aug. 16, 1994

[54] TRIAZOLYL, TETRAZOLYL AND AZIDO-SUBSTITUTED FATTY ACID ANALOG ENZYME SUBSTRATES

[75] Inventors: Balekudru Devadas, St. Louis; Jeffrey I. Gordon, Olivette; Steven P. Adams, St. Charles, all of Mo.

[73] Assignee: Washington University, St. Louis, Mo.

[21] Appl. No.: 963,620

[22] Filed: Oct. 20, 1992

Related U.S. Application Data

[63] Continuation of Ser. No. 596,183, Oct. 12, 1990, abandoned.

[51] Int. Cl.$^5$ .................. C07D 257/04; C07D 255/02; C07C 117/08
[52] U.S. Cl. ........................................ 548/253; 552/1; 548/261; 548/268.6
[58] Field of Search ...................... 548/253, 261, 268.6; 514/381, 383, 579

[56] References Cited

U.S. PATENT DOCUMENTS 4,340,728 7/1982 Endo et al. ........................... 536/23
4,496,577 1/1985 Muchowski et al. ................ 514/392

FOREIGN PATENT DOCUMENTS 327523 8/1989 European Pat. Off. ... C07C 59/125

OTHER PUBLICATIONS

Hibbs & Marzuki, Biochim. Biophys. Acta 862, 445–450 (1986).
Heuckeroth et al., J. Biol. Chem. 263, 2127–2133 (1988).
Heuckeroth et al., Proc. Natl. Acad. Sci. USA 85, 8795–8799 (1988).
Heuckeroth et al., Proc. Natl. Acad. Sci. USA 86, 5262–5266 (1989).
Ratner et al., Proc. Natl. Acad. Sci. USA 86, 8655–8659 (1989).

*Primary Examiner*—David B. Springer
*Attorney, Agent, or Firm*—Scott J. Meyer

[57] ABSTRACT

Azido-substituted fatty acid analogs which are useful in the fatty acid acylation of peptides and proteins and as antiviral agents are disclosed having the following chemical structure:

$$Z-(CH_2)_x COOR$$

wherein
  Z = azido, tetrazolyl or triazolyl
  R = H or $C_1$-$C_8$ alkyl, and
  x = 8–12.

15 Claims, No Drawings

TRIAZOLYL, TETRAZOLYL AND AZIDO-SUBSTITUTED FATTY ACID ANALOG ENZYME SUBSTRATES

This invention was made with Government support under Grant No. AI 27179 awarded by the National Institutes of Health. The Government has certian rights in the invention.

This is a continuation of application Ser. No. 07/596,183, filed Oct. 12, 1990, abandoned.

BACKGROUND OF THE INVENTION

This invention relates to biologically active fatty acid analog substrates of myristoylating enzymes and, more particularly, to azido-substituted fatty acid analogs which are useful in the fatty acid acylation of peptides and proteins.

Fatty acid acylation of specific eukaryotic proteins is a well established process which can conveniently be divided into two categories. On the one hand, palmitate ($C_{16}$) is linked to membrane proteins via ester or thioester linkage post-translationally.

On the other hand, it is known that myristate ($C_{14}$) becomes covalently bound to soluble and membrane proteins via amide linkage early in the protein biosynthetic pathway. In the N-myristoylated proteins, amino-terminal glycine residues are known to be the site of acylation.

A variety of vital and cellular proteins have been shown to be thus modified by the covalent attachment of myristate linked through an amide bound to glycine at their amino termini. An example of a most thoroughly studied myristoylated protein is the transforming protein of Rous sarcoma virus, p60[v-src].

The myristoylation reaction can be represented as follows:

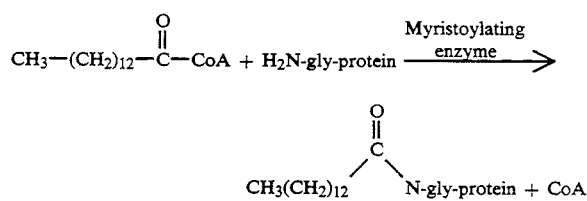

Further background information on the above protein fatty acid acylation can be had by reference to the following series of articles by scientists associated with the Washington University School of Medicine:

Towler and Glaser, *Biochemistry* 25, 878–84 (1986);

Towler and Glaser, *Proc. Natl. Acad. Sci. USA* 83, 2812–2816 (1986);

Towler et al., *Proc. Natl. Acad. Sci, USA* 84, 2708–2712 (1987);

Towler et al., *J. Biol. Chem.* 262, 1030–1036 (1987);

Towler et al., *Ann. Rev. Biochem.* 57, 69–99 (1988);

Heuckeroth et al., *Proc. Natl. Acad. Sci. USA* 85, 8795–8799 (1988); and

Heuckeroth and Gordon, *Proc. Natl. Acad. Sci. USA* 86, 5262–5266 (1989).

Unique synthetic peptides having relatively short amino acid sequences which are useful as substrates of myristoylating enzymes are described in U.S. Pat. Nos. 4,740,588 and 4,778,878. Examples of such peptides are

Gly—Asn—Ala—Ala—Ala—Ala—Arg—Arg and
Gly—Asn—Ala—Ala—Ser—Tyr—Arg—Arg.

Certain other unique synthetic peptides are inhibitors of myristoylating enzymes as described in U.S. Pat. Nos. 4,709,012 and 4,778,877.

BRIEF DESCRIPTION OF THE INVENTION

In accordance with the present invention, biologically active fatty acid analog substrates for myristoylating enzymes are provided. These compounds are azido- or azido-like-substituted fatty acid analogs which can also contain oxygen and/or sulfur heteroatoms in the fatty acid backbone. They are useful in the fatty acid acylation of peptides and proteins. The preferred fatty acid analogs can be represented by the following two groups of chemical structures:

$$Z-(CH_2)_x \, COOR \qquad (I)$$

wherein
Z = azido, tetrazolyl or triazolyl,
R = H or $C_{1-8}$ alkyl, and
x = 8–12.

$$\text{Compounds of structure I} \qquad (II)$$

in which a methylene group from carbon position 3 to within 2 carbons of Z is replaced by oxygen or sulfur. The carboxyl carbon atom is defined in this structure as number 1 based on conventional nomenclature.

These novel substrate compounds are useful for studying the regulation of enzyme action in fatty acid acylation and the role of N-myristoylation in protein function. They can serve as synthetic substrates for the N-myristoylating enzymes in sources such as yeasts, fungi, wheat germ lysates and mammalian cells. These novel compounds differ in hydrophobicity from myristic acid while maintaining approximately the same chain length. Thus, when incorporated into myristoyl-proteins, they should alter the acylprotein's subsequent interactions with membranes or with other proteins. They alos have potential use as antiviral, antifungal and antineoplastic agents.

Illustrative examples of the biologically active azido-substituted fatty acid analogs of this invention are:

| Name | Compound No. |
|---|---|
| 12-Azidododecanoic acid | (1) |
| 11-Azidoundecanoic acid | (2) |
| 9-Azidononanoic acid | (3) |
| 13-Azidotridecanoic acid | (7) |
| 5-(1-Azido-hexane-6-thia)pentanoic acid | (13) |
| 2-(1-Azido-nonane-9-thia)acetic acid | (19) |
| 4-(1-Azido-octane-6-thia)propionic acid | (23) |
| 9-(1-Azido-ethane-2-oxa)nonanoic acid | (40) |
| 8-(1-Azido-propane-3-oxa)octanoic acid | (41) |
| 5-(1-Azido-hexane-6-oxa)pentanoic acid | (42) |
| 2-(1-Azido-nonane-9-oxa)acetic acid | (43) |
| 12-(Tetrazolyl)dodecanoic acid | (46) |
| 12-[1,2,4]-Triazolyl)dodecanoic acid | (48) |
| 12-(N-2-[1,2,3]-Triazolyl)dodecanoic acid | (50) |

DETAILED DESCRIPTION OF THE INVENTION

The azido-substituted fatty acid analogs of this invention can be prepared by various reaction schemes. For example, in one scheme an ω-iodocarboxylic acid having the desired fatty acid chain length can be reacted with azide ion, e.g. potassium or sodium azide, and 18-Crown-6 in organic solvent medium, e.g., DMF, at normal room temperature. The preparation of the reagent, 18-Crown-6, is described by Gokel et al., *Org. Syn.* 57, 30 (1977).

The azido-substituted fatty acid analogs containing oxygen and/or sulfur heteroatoms in the fatty acid backbone can be synthesized by first preparing the oxygen and/or sulfur heteroatom-substituted fatty acid followed by derivatization with the azide ion. Preparation of oxa- and thia-substituted fatty acids can be carried out by methods analogous to the preparation of mixed ethers by the Williamson synthesis under phase transfer conditions. For example, an appropriate ω-bromo carboxylic acid or ester can be reacted with an alcohol or an alkyl thiol to produce, respectively, the oxa-substituted fatty acid ether or the thia-substituted fatty acid ether.

The preparation of the azido substituted fatty acid analogs of the invention are preferably carried out by the following illustrative reaction Schemes:

SCHEME I

I—(CH$_2$)$_x$COOH $\xrightarrow[\text{DMF, RT, 16 h}]{\text{NaN}_3\text{, 18-Crown-6}}$ N$_3$—(CH$_2$)$_x$COOH 1  x = 11
2  x = 10
3  x = 8

SCHEME II

HO—(CH$_2$)$_{12}$COOH $\xrightarrow[\text{CCl}_4\text{, RT, 16 h}]{\text{(Me)}_3\text{SiI}}$

[I—(CH$_2$)$_{12}$COO—(CH$_2$)$_{12}$COOH] $\xrightarrow[\text{THF, RT, 16 h}]{\text{1N NaOH}}$
5

I—(CH$_2$)$_{12}$COOH $\xrightarrow[\text{DMF, RT, 16 h}]{\text{NaN}_3\text{, 18-Crown-6}}$ N$_3$(CH$_2$)$_{12}$COOH
6  7

SCHEME III

THP—O—(CH$_2$)$_6$I $\xrightarrow[\substack{\text{DMF, 18-Crown-6}\\\text{RT, 2 h}}]{\text{KSCOCH}_3}$
8

THP—O—(CH$_2$)$_6$—SCOCH$_3$ $\xrightarrow[\substack{50\% \text{ NaOH, Toluene}\\(\text{Bu})_4\text{NHSO}_4\text{, RT, 3 h,}\\60°\text{ C., 1 h}}]{\text{Br(CH}_2)_4\text{COOBu}^t}$
9

THP—O—(CH$_2$)$_6$S(CH$_2$)$_4$COOBu$^t$ $\xrightarrow[\text{MeOH, RT, 2 h}]{p\text{-TSA}}$
10

HO—(CH$_2$)$_6$S(CH$_2$)$_4$COOBu$^t$ $\xrightarrow[\text{CH}_3\text{CN, RT}]{\text{(PhO)}_3\text{PMeI}}$
11

I—(CH$_2$)$_6$S(CH$_2$)$_4$COOBu$^t$ $\xrightarrow[\substack{\text{2. NaN}_3\text{, 18-Crown-6}\\\text{DMF, RT, 16 h}}]{1.\ (\text{Me})_3\text{SiI, CCl}_4}$
12

N$_3$(CH$_2$)$_6$S(CH$_2$)$_4$COOH
13

SCHEME IV

THPO(CH$_2$)$_9$I $\xrightarrow[\text{CH}_3\text{CN, Et}_3\text{N}]{\text{HSCH}_2\text{COOMe}}$
14  RT, 2 h THPO(CH$_2$)$_9$SCH$_2$COOMe $\xrightarrow[\text{MeOH, RT, 2 h}]{p\text{-TSA}}$
15

HO(CH$_2$)$_9$SCH$_2$COOMe $\xrightarrow[\text{CH}_2\text{Cl}_2\text{RT, 2.5 h}]{\text{(PhO)}_3\text{PMeI}}$
16

I(CH$_2$)$_9$SCH$_2$COOMe $\xrightarrow[\text{DMF, RT, 16 h}]{\text{NaN}_3\text{, 18-Crown-6}}$
17

N$_3$(CH$_2$)$_9$SCH$_2$COOMe $\xrightarrow[\substack{\text{MeOH, THF}\\\text{RT, 4 h}}]{\text{1N NaOH}}$ N$_3$(CH$_2$)$_9$SCH$_2$COOH
18  19

SCHEME V

I—(CH$_2$)$_8$I + HS—(CH$_2$)$_2$COOH $\xrightarrow[\text{CH}_3\text{CN, RT, 16 h}]{\text{Et}_3\text{N}}$
20  21

I—(CH$_2$)$_8$S(CH$_2$)$_2$COOH $\xrightarrow[\substack{\text{DMF, 18-Crown-6}\\\text{RT, 16 h}}]{\text{NaN}_3}$
22

N$_3$(CH$_2$)$_8$S(CH$_2$)$_2$COOH
23

SCHEME VI

THPO(CH$_2$)$_x$OH + Br(CH$_2$)$_y$COOBu$^t$ $\xrightarrow[\substack{50\% \text{ NaOH}\\\text{Toluene, RT}}]{(\text{Bu})_4\text{NHSO}_4}$ 24 x = 2, y = 8    28 y = 8
25 x = 3, y = 7    29 y = 7
26 x = 6, y = 4    30 y = 4
27 x = 9, y = 1    31 y = 1

THPO(CH$_2$)$_x$O(CH$_2$)$_y$COOBu$^t$ $\xrightarrow[\substack{2.\ (\text{PhO})_3\text{PMeI}\\\text{CH}_2\text{Cl}_2\text{, RT, 4 h}}]{1.\ p\text{-TSA, MeOH, RT, 1 h}}$ 32 x = 2, y = 8
33 x = 3, y = 7
34 x = 6, y = 4
35 x = 9, y = 1

I(CH$_2$)$_x$O(CH$_2$)$_y$COOBu$^t$ $\xrightarrow[\substack{2.\ \text{NaN}_3\text{, DMF}\\\text{18-Crown-6, RT}}]{1.\ (\text{Me})_3\text{SiI, CCl}_4}$ 36 x = 2, y = 8
37 x = 3, y = 7
38 x = 6, y = 4
39 x = 9, y = 1

N$_3$(CH$_2$)$_x$O(CH$_2$)$_y$COOH 40 x = 2, y = 8
41 x = 3, y = 7
42 x = 6, y = 4
43 x = 9, y = 1

SCHEME VII

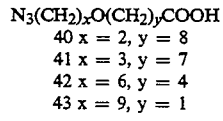 + I(CH$_2$)$_{11}$COOH $\xrightarrow[55°\text{ C., 1.5 h}]{\substack{\text{NaH}\\\text{DMF, 18-Crown-6}}}$
44                45

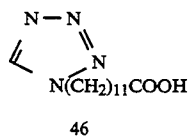
46

SCHEME VII (continued)

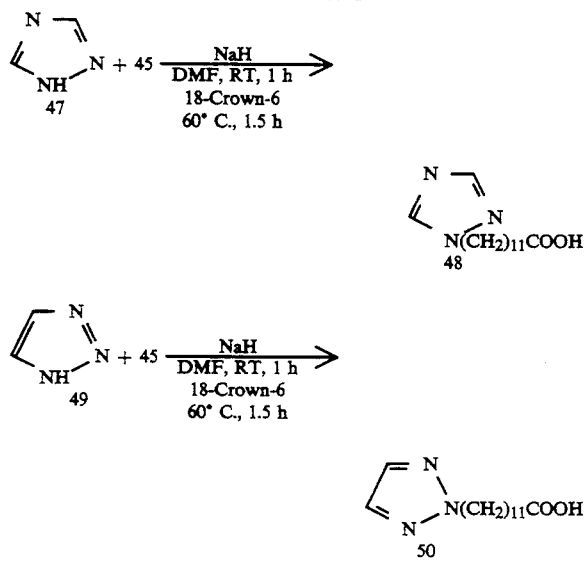

The following examples will further illustrate the invention although it will be appreciated that the invention is not limited to these specific examples. Examples 1 to 32 illustrate the synthesis of compounds according to the Reaction Schemes I to VII set forth hereinbefore. Example 33 illustrates the biological testing of representative compounds thus synthesized in (A) an in vitro yeast N-myristoyltransferase (NMT) assay and (B) a human cell culture assay to measure inhibitory activity against human immunodeficiency virus (HIV). In these examples, 18-Crown-6 refers to 1,4,7,10,13,16-hexaoxacyclooctadecane, THP refers to tetrahydropyran, THF refers to tetrahydrofuran, DMF refers to dimethylformamide and DMSO refers to dimethylsulfoxide.

EXAMPLE 1

12-AZIDODODECANOIC ACID (1). A mixture of 12-iodododecanoic acid (2.1 g, 0. 0064 mol), sodium azide (1.2 g, 0.019 mol) and 18-crown-6 (0.5 g, 0.0019 mol) in dimethylformamide (25 ml) was stirred at room temperature for 16 h. After removal of the solvent under vacuum, the residue was partitioned between 1N HCl (25 ml) and dichloromethane (25 ml). The organic phase was washed with water (3×25 ml), dried (Na$_2$SO$_4$) and concentrated to give a pale yellow liquid (3 g) which was purified by flash chromatography (silica gel) using 15% ethylacetate in hexane to give 12-azidododecanoic acid (1.3 g, 84%) as a colorless liquid. $^1$H NMR (CDCl$_3$) δ: 3.19 (t, 2H, J=6.9 Hz, CH$_2$); 2.28 (t, 2H, J=7.5 Hz, CH$_2$); 1.53 (m, 4H, 2×CH$_2$); 1.21 (m, 14H), FABMS (m/z): 254 (M+2Li-H); 248 (M+Li) and 226.

EXAMPLE 2

11-AZIDOUNDECANOIC ACID (2). The title compound was prepared in a similar manner as described for 1 except that 11-iodoundecanoic acid was substituted for an equivalent amount of 12-iodododecanoic acid. Yield 64%. $^1$H NMR (CDCl$_3$) δ: 3.28 (t, 2H, J=6.8 Hz, CH$_2$); 2.35 (t, 2H, J=7.7 Hz, CH$_2$); 1.6 (m, 4H); 1.29 (m, 1.29 (m, 12H, —CH$_2$), FABMS, m/z: 228 (M+H); 200 and 182.

EXAMPLE 3

9-AZIDONONANOIC ACID (3). The title compound was prepared in a similar manner as described for 1 except that 9-iodononanoic acid was substituted for an equivalent amount of 12-iodododecanoic acid. Yield 77%. $^1$H NMR (CDCl$_3$) δ:3.26 (t, 2H, J=7.00 Hz); 2.36 (t, 2H, J=5.4 Hz); 1.62 (m, 4H); 1.33 (m, 8H), FABMS. m/z: 212 (M+H) and 206 (M+Li).

EXAMPLE 4

12-IODOTRIDECANOIC ACID (6). A mixture of 12-hydroxytridecanoic acid 4 (0.3 g, 0.0013 mol, and iodotrimethylsilane (0.5 ml) in carbontetrachloride (3 ml) was stirred at room temperature for 16 h. The solution was concentrated, cold water (10 ml) was added and the mixture was extracted with ethyl acetate (2×10 ml). The organic phase was washed with water (2×15 ml), dried (Na$_2$SO$_4$) and concentrated under reduced pressure. The resulting residue was purified by flash chromatography (silica gel) using 15% ethylacetate in hexane to give intermediate compound 5 (0.2 g) as a pale yellow solid. FABMS: m/z, 565 (M+2Li-H), 559 (M+Li). 5 (0.2 g) was subjected to basic hydrolysis by stirring in 1N NaOH (3 ml) and THF (2 ml) at room temperature for 16 h. The solution was cooled, acidified with 2N HCl (1.5 ml) and extracted with ethylacetate (2×10 ml). The organic phase was washed with water (2×10 ml), dried (Na$_2$SO$_4$), concentrated under reduced pressure and the residue was purified by flash chromatography (silical gel) using 10% ethylacetate in hexane to give the title compound 6 (0.15 g, 34%). $^1$H NMR (CDCl$_3$) δ: 3.19 (t, 2H, J=6.9 Hz); 2.35 (t, 2H, J=7.5 Hz); 1.85 (m, 2H); 1.64 (m, 2H), 1.27 (m, 16H); FABMS: m/z, 353 (M+2Li-H); 347 (M+Li) and 225. HRMS: M/Z, C$_{13}$H$_{25}$IO$_2$Li, calc.: 275.2059; found: 275.2004 (M+Li).

EXAMPLE 5

13-AZIDOTRIDECANOIC ACID (7). A mixture of 6 (0.15 g, 0.44 mmol) sodium azide (0.09 g, 1.4 mmol) and 18-crown-6 (0.015 g, 0.057 mmol) in dimethylformamide (3 ml) was stirred at room temperature for 16 h. DMF was distilled under vacuum, cold 2N HCl (2 ml) was added and the mixture was extracted with ethylacetate (10 ml). The organic phase was washed with water (2×10 ml), dried (Na$_2$SO$_4$) and concentrated under reduced pressure to give a pale yellow solid which was purified by flash chromatography (silica gel) using 20% ethylacetate in hexane to afford the title compound 7 (0,075 g, 67%) as a white solid. $^1$H NMR (CDCl$_3$) δ: 3.26 (t, 2H, J=6.9 Hz); 2.35 (t, 2H, J=7.5 Hz); 1.62 (m, 4H); 1.35 (m, 14H), FABMS: (m/z); 256 (M+H); 230 and 210. HRMS C$_{13}$H$_{25}$N$_3$O$_2$ Li calc.: 262.2107, found: 262.2164 (M+Li).

EXAMPLE 6

1-(TETRAHYDROPYRANLOXY) -6-THIOACETYL HEXANE (9 ). To a solution of potassium thioacetate (0.34 g, 0.003 mol) and 18-crown-6 (0.16 g, 0.0006 mol) in DMF (5 ml), was added a solution of THP—O—(CH$_2$)$_6$I 8 (0.7 g, 0.0022 mol) in DMF (2 ml). The reaction mixture was stirred at room temperature for 2 h, DMF was distilled under vacuum and the residue was partitioned between water (25 ml) and dichloromethane (25 ml). The organic phase was washed with water (2×10 ml), dried (Na$_2$SO$_4$) and concentrated. The resulting material was purified by flash chromatography (silica gel) using 10% ethylacetate in hexane to give the title compound 9 (0.5 g, 86%) as a colorless liquid. $^1$H NMR (CDCl$_3$) δ: 4.57 (m, 1H); 3.75 (m, 2H); 3.45 (m, 2H); 2.87 (t, 2H); 2.32 (s, 3H, —COCH$_3$); 1.75 (m, 2H); 1.6 (m, 8H); 1.39 (m, 4H), FABMS: m/z, 267 (M+Li) and 183.

EXAMPLE 7 t-BUTYL-5-(1-TETTRAHYDROPYRANYLOXY-HEXANE-6-THIA) PENTANOATE(10). A mixture of 9(0.45 g, 0.0017 mol), t-butyl-5-bromovalerate (0.49 g, 0.002 mol) and tetrabutylammonium hydrogen sulphate (0.25 g, 0.70 mol) was stirred vigorously in 50% sodium hydroxide (0.8 ml), toluene (2.0 ml) and THF (2.0 ml) at room temperature for 3 h and at 60° C. for 1 h. The reaction mixture was poured into ice and diluted with water (10 ml). The organic phase was washed with water (3×15 ml), dried (Na$_2$SO$_4$) and concentrated to give a thick syrup, which was purified by flash chromatography (silica gel) using 10% ethyl acetate in hexane to afford the title compound 10 (0.65 g, 90%) as a colorless oil. $^1$H NMR (CDCl$_3$) δ: 4.57 (m, 1H); 3.8 (m, 2H); 3.45 (m, 2H); 2.51 (m, 2H); 2.23 (t, 2H); 1.6 (m, 12H), 1.44 (s, 9H); 1.4 (m, 8H), FABMS: m/z, 381 (M+Li); 325, 241 and 217.

EXAMPLE 8 t-BUTYL-5-(1-HYDROXY HEXYL-6-THIA)PENTANOATE (11). A solution of 10 (0.65 g, 0.0017 mol) in methanol (5 ml), containing p-toluenesulfonic acid (0.1 g, 0.53 mmol) was stirred at room temperature for 2 h. To this solution was added sodium bicarbonate (0.15 g) and the mixture was concentrated under reduced pressure. The residue was purified by flash chromatography (silica gel) using 15% ethylacetate in hexane to give the title compound 11 (0.36 g, 71%) as a colorless syrup. $^1$H NMR (CDCl$_3$) δ: 3.65 (q, 2H); 2.51 (t, 4H); 2.23 (t, 2H); 1.6 (m, 8H); 1.44 (s, 9H); 1.40(m, 4H); 1.25 (t, 1H, —OH), FABMS: m/z, 297(M+Li); 241 and 195.

EXAMPLE 9 t-BUTYL-5-(1-IODO-HEXANE-6-THIA) PENTANOATE (12). A mixture of 11 (0.35 g, 0.0012 mol) and methyltriphenoxyphosphonium iodide (0.7 g, 0.0015 mol) in acetonitrile (5 ml) was stirred at room temperature for 2.5 h. After removal of the solvent, the residue was dissolved in dichloromethane (25 ml) and a cold solution of 0.5N NaOH was added. The organic phase was washed with water (3×15 ml), dried (Na$_2$SO$_4$), concentrated under reduced pressure and the residue was purified by flash chromatography using 3% ethylacetate in hexane to yield the title compound 12 (0.49, 83%) as a colorless liquid. $^1$H NMR (CDCl$_3$) δ: 3.39 (m, 4H); 3.19 (t, 2H); 2.34 (t, 2H); 1.75 (m, 2H); 1.6 (m, 6H); 1.44 (s, 9H); 1.39 (m, 4H), FABMS: m/z, 407 (M+Li); 401 (M+H); 345, 327 and 217.

EXAMPLE 10

5-(1-AZIDO-HEXANE-6-THIA) PENTANOIC ACID (13). A mixture of 12 (0.36 g, 0.9 mmol) and iodotrimethylsilane (0.2 ml) in carbontetrachloride (3.0 ml) was stirred at room temperature for 4 h. The solution was cooled, cold water (10 ml) was added and the mixture extracted with carbontetrachloride (2×5 ml). The organic phase was successively washed with 5% sodium sulphite (5 ml), water (3×10 ml) and dried (Na$_2$SO$_4$). The solution was concentrated under reduced pressure and dried under vacuum to give 0.16 g of a thick syrup. This product was dissolved in dimethylformamide (2 ml), to which was added sodium azide (0.096 g, 0.0015 mol) and 18-crown-6 (0.01 g) and then stirred at room temperature for 16 h. The solvent was distilled under vacuum, 1N HCl (10 ml) was added and the mixture was extracted with ethylacetate (2×10 ml). The organic phase was washed with water (2×10 ml), dried (Na$_2$SO$_4$), concentrated and the residue was purified by flash chromatography (silica gel) using 15% ethylacetate in hexane to afford the title compound 13 (0.07 g, 58%) as a colorless liquid. $^1$H NMR (CDCl$_3$) δ: 3.27 (t, 2H); 2.51 (m, 4H); 2.39 (t, 2H); 1.7 (m, 8H); 1.4 (m, 4H), FABMS: m/z, 272 (M+2Li-H); 266 (M+Li) and 244. HRMS: m/z, C$_{11}$H$_{21}$N$_3$SO$_2$Li, calc: 266.1516, found: 266.1491 (M+Li).

EXAMPLE 11

METHYL L-2-(1-TETRAHYROPYRANYLOXY-NONANE-9-THIA)ACETATE (15). To a solution of THP—O—(CH$_2$)$_9$I 14 (0.23 g, 0.65 mmol) and methyl thioglycolate (0.1 g, 0.94 mmol) in acetonitrile, was added triethylamine (0.17 ml, 1.2 mmol) was added and the mixture was stirred at room temperature for 2 h. The solution was concentrated, water (10 ml) was added and the mixture was extracted with ethylacetate (2×10 ml). The organic phase was washed with water (2×10 ml), dried (Na$_2$SO$_4$), concentrated under reduced pressure and the residue was purified by flash chromatography (silica gel) using 5% ethylacetate in hexane to give the title compound 15 (0.2 g, 92%) as a colorless oil. $^1$H NMR (CDCl$_3$) δ: 4.57 (m, 1H); 3.85 (m, 1H), 3.74 (s, 3H); 3.71 (m, 1H); 3.5 (m, 1H); 3.4 (m, 1H); 3.2 (s, 2H, —OCH$_2$), 2.62 (t, 2H); 1.75 (m, 2H); 1.57 (m, 8H); 1.3 (m, 10H). FABMS; m/z, 339 (M+Li); 249 and 231.

EXAMPLE 12

METHYL-2-(1-HYDROXYNONANE-9-THIA)ACETATE (16). The tetrahydropyranyl group in 15 (0.2 g, 0.6 mmol) was cleaved using p-toluenesulfonic acid in a similar manner as described for cleavage of the THP group in 10 in Example 8 to provide the title compound 16 Yield 0.14 g (93%). $^1$H NMR (CDCl$_3$) δ: 3.74 (s, 3H, OCH$_3$); 3.65 (q, 2H); 3.23 (s, 2H, —OCH$_2$); 2.63 (t, 2H); 1.6 (m, 4H); 1.3 (m, 10H); 0.9 (t, 1H). FABMS: m/z, 255 (M+Li).

EXAMPLE 13

METHYL-2-(1-IODO-NONANE-9-THIA)ACETATE (17). The title compound 17 was prepared by the iodination of 16 (0.27 g, 1.1 mmol) using methyltriphenoxyphosphonium iodide in a manner similar to that described for the preparation of 12 in Example 9. Yield 0.24 g, 62%. $^1$H NMR (CDCl$_3$) δ: 3.74 (s, 3H, OCH$_3$); 3.23 (s, 2H, —OCH$_2$); 3.19 (t, 2H); 2.63 (t, 2H); 1.82 (m, 2H); 1.60 (m, 2H); 1.33 (m, 10H). FABMS: m/z, 365 (M+Li), 359 (M+H) and 237.

EXAMPLE 14

METHYL-2-(1-AZIDONONANE-9-THIA)ACETATE (18). A mixture of 17 (1.5 g, 4.2 mmol), sodium azide (0.5 g, 7.7 mmol) and 18-crown-6 (0.12 g, 0.45 mmol) in dimethylformamide (5 ml) was stirred at room temperature for 16 h. The solution was concentrated under high vacuum and the residue was partitioned between water (10 ml) and dichloromethane (15 ml). The organic phase was washed with water (3×10 ml), dried ($Na_2SO_4$), concentrated and the residue was purified by flash chromatography using 5% ethylacetate in hexane to furnish the title compound 18 (1.04 g, 83%) as a colorless liquid. $^1$H NMR ($CDCl_3$) δ: 3.74 (s, 3H, $OCH_3$); 3.26 (t, 2H); 3.23 (s, 2H, $OCH_2$); 2.63 (t, 2H); 1.59 (m, 4H); 1.31 (m, 10H). FABMS: m/z, 280 (M+Li) and 252.

EXAMPLE 15

2-(1-AZIDONONANE-9-THIA)ACETIC ACID (19). A solution of 18 (0.54 g, 2 mmol) in 1N methanolic sodium hydroxide (8 ml) and THF (2 ml) was stirred at room temperature for 4 h. The reaction mixture was concentrated to dryness, water (10 ml) was added, and the mixture was neutralized with 2N HCl (4 ml) and extracted with dichloromethane (2×10 ml). The organic layer was washed with water (2×10 ml), dried ($Na_2SO_4$), concentrated and the residue was purified by flash chromatography using 25% ethylacetate in hexane to afford the title compound 19 (0.4 g, 78%) as a colorless liquid. $^1$H NMR ($CDCl_3$) δ: 3.28 (t, 2H); 3.28 (s, 2H, —$OCH_2$); 69 (t, 2H); 1.63 (m, 4H); 1.38 (m, 10H) $^{13}$C NMR ($CDCl_3$) δ: 26.62, 28.59, 28.77, 28.81, 28.97, 29.24, 32.74, 33.47, 51.42 and 176.95. FABMS: (m/z), 272 (M+2Li-H); 266 (M+Li); 244 and 238. HRMS: m/z, $C_{11}H_{21}N_3O_2Li$, calc: 266.1516, found: 266.1502 (M+Li).

EXAMPLE 16

4-(1-IODOOCTANE-8-THIA)PROPIONIC ACID (22). A mixture of diiodooctane 20 (2.8 g, 7.65 mmol), 3-mercaptopropionic acid 21 (0.75 ml, 8.6 mmol), dimethylaminopyridine (0.1 g, 0.82 mmol) and triethylamine (2.4 ml, 17.1 mmol) in acetonitrile (20 ml) was stirred at room temperature for 16 h. After removal of the solvent under reduced pressure, the residue was partitioned between 1N HCl (25 ml) and dichloromethane (25 ml). The organic phase was washed with water (3×15 ml), dried ($Na_2SO_4$), concentrated under reduced pressure and the residue was purified by flash chromatography (silica gel) using 20% ethylacetate in hexane to give the title compound 22 (0.3 g, 11%) as a low melting solid. $^1$H NMR ($CDCl_3$) δ: 3.19 (t, 2H, 6.9 Hz); 2.78 (m, 2H); 2.66 (m, 2H); 2.54 (m, 2H); 1.82 (m, 2H); 1.6 (m, 2H); 1.33 (m, 8H). FABMS: m/z, 357 (m+2Li-H); 351 (M+Li); 223 (M+Li-HI). HRMS: m/z, $C_{11}H_{21}IO_2SLi$, calc: 351.0467, found: 351.0484 (M+Li).

EXAMPLE 17

4-(1-AZIDOOCTANE-6-THIA)PROPIONIC ACID (23). The title compound 23 was obtained by stirring a solution of 22 in DMF containing sodium azide and 18-crown-6 in a similar manner as described for the preparation of compound 1 in Example 1. Yield 66%. $^1$H NMR ($CDCl_3$) δ: 3.26 (t, 2H); 2.77 (t, 2H); 2.67 (t, 2H); 2.54 (t, 2H); 1.59 (m, 4H); 1.33 (m, 8H). 13C NMR ($CDCl_3$) δ: 26.58; 26.60; 28.66; 28.77; 28.97; 28.99; 29.41; 32.13; 34.69; 51.42, 178.15. FABMS: m/z, 272 (M+Li-H); 266 (M+Li); 244 and 229. HRMS: m/z, $C_{11}H_{21}N_3O_2SLi$, calc: 266.1516, found: 266.1510 (M+Li).

EXAMPLE 18 t-BUTYL-9-(1-TETRAHYDROPYRANYLOXY-ETHANE-2-OXA) NONANOATE (32). A mixture of 24 (0.97 g, 0.0066 mol) and 28 (1.2 g, 0.004 mol) in 50% aqueous NaOH (2.7 ml) and toluene (3.0 ml) containing tetrabutylammoniumhydrogen sulfate (0.25 g, 0.74 mmol) was stirred at room temperature for 16 h. The reaction mixture was poured into cold water (15 ml) and extracted with ethylacetate (3×15 ml). The organic phase was washed with water (3×15 ml), dried ($Na_2SO_4$) and concentrated under reduced pressure to give 1.5 g of liquid which was purified (twice) by flash chromatography (silica gel) using 10% EtOAc in hexane containing 0.2% $Et_3N$ to give 0.73 g (50%) of the title compound 32 as a colorless liquid. $^1$H NMR ($CDCl_3$) δ: 4.64 (m, 1H); 3.85 (m, 2H); 3.60 and 3.47 (m, 6H); 2.19 (t, 2H, J=7.2 Hz); 1.8 (m, 2H); 1.56 (m, 8H); 1.44 (s, 9H); 1.29 (bs, 8H). FABMS: m/z, 365 (M+Li), 309, 225 and 201.

EXAMPLE 19 t-BUTYL-8-(1-TETRAHYDROPYRANYLOXY-PROPANE-3-OXA)-OCTANOATE (33). The title compound 33 was prepared from 25 and 29 in a manner similar to the preparation of 32 in Example 18. Yield 41%. $^1$H NMR ($CDCl_3$) δ: 4.58 (m, 1H); 3.83 (m, 2H); 3.52, 3.40 (2m, 6H); 2.22 (t, 2H); 1.86 (m, 2H); 1.55 (m, 10H); 1.44 (s, 9H); 1.31 (m, 6H). FABMS: m/z=365 (M+Li), 309 and 275. HRMS: m/z, $C_{20}H_{38}O_5Li$, calc: 365.2879, found: 365.2870 (M+Li).

EXAMPLE 20 t-BUTYL-5-(1-TETRAHYDROPYRANYLOXY-HEXANE-6-OXA-PENTANOATE (34). To an ice-cold solution of 26 (0.7 g, 0.0035 mol) and t-butyl-5-bromovalerate 30 (0.6 g, 0.0029 mol) in toluene (2 mL), 50% aq. NaOH solution (1.4 mL) and tetrabutylammonium hydrogen sulfate (0.12 g, 0.35 mmol) were added. The resulting mixture was stirred for 30 min. at 0° C. and then for 4 h at room temperature. The reaction was poured into 10 mL of ice-water and extracted with EtOAc (2×15 mL). The organic phase was washed with water (3×15 mL), dried ($Na_2SO_4$) and concentrated in vacuo to afford a pale, yellow liquid (1.1 g) which was purified by flash chromatography using 20% EtOAc in hexane containing 0.2% $Et_3N$ as the eluent. The unreacted bromovalerate 30 (0.31 g, 46%) eluted first, followed by the title compound 34. The chromatography fractions containing 12 were combined, concentrated, and dried under high vacuum to afford 0.34 g of 34 (32%) as a colorless oil. $R_f$0.63 (50% EtOAc in hexane). $^1$H NMR, 4.56 (t, 1H); 3.87 (m, 1H); 3.75 (m, 1H); 3.39 (m, 6H); 2.24 (t, 2H), 1.3–1.9 (m, 27H). FABMS: m/z 376 (M+$NH_4$). HRMS: m/z, $C_{20}H_{38}O_5Li$, calc: 365.2879, found: 365.2901.

EXAMPLE 21 t-BUTYL-2-(1-TETRAHYDROPYRANYLOXY-NONANE-9-OXA)ACETATE (35). The title compound was prepared in a manner similar to the preparation of compound 32 in Example 18. Yield 64%.

$^1$H NMR ($CDCl_3$) δ: 4.58 (m, 1H); 3.9 (s, 2H); 3.85 and 3.75 (m, 2H); 3.5 (t, 2H); 3.39 (m, 2H); 1.58 (m, 10H); 1.48 (s, 9H); 1.31 (m, 10H). FABMS: m/z=365 (M+Li), 309 and 225.

EXAMPLE 22 t-BUTYL-9-(1-IODO-ETHANE-2-OXA)-NONANOATE (36). A solution of 32 (0.7 g, 2.0 mmol) in methanol (3 ml) containing p-toluenesulfonic acid (0.1 g, 0.53 mmol) was stirred at room temperature for 1 h, $NaHCO_3$ (0.1 g) was added and the mixture was concentrated. The residue was purified by flash chromatography (silica gel) using 25% EtOAc in hexane to give 0.52 g of a colorless liquid. This product was dissolved in acetonitrile (7 ml), methyltriphenoxy phosphonium iodide (1.15 g, 2.5 mmol) was added and the mixture was stirred at room temperature for 4 h. The reaction mixture was concentrated to dryness, water (15 ml) was added and the mixture was extracted with ethylacetate (3×15 ml). the organic phase was washed with 5% sodium thiosulphate (10 ml) water (3×15 ml), dried ($Na_2SO_4$) and concentrated. The residue was purified by flash chromatography (silica gel) using 4% ethylacetate in hexane to give the title compound 36 (0.46 g, 66%) as a colorless liquid.

$^1$H NMR ($CDCl_3$) δ: 3.68 (t, 2H); 3.47 (t, 2H); 3.25 (t, 2H); 2.2 (t, 2H); 1.55 (m, 4H); 1.44 (s, 9H); 1.31 (m, 8H). FABMS: m/z=391 (M+Li), 335, 329 and 253. HRMS: m/z, $C_{15}H_{29}IO_3Li$, calc. 391.1322, found 391.1364 (M+Li).

EXAMPLE 23 t-BUTYL-8-(1-IODO-PROPANE-3-OXA)OCTANOATE (37). The title compound 37 was prepared from 33 in a manner similar to the preparation of compound 36 in Example 22. Yield 65%. $^1$H NMR ($CDCl_3$) δ: 3.44 (m, 4H); 3.28 (t, 2H J=6.9 Hz); 2.2 (t, 2H, J=7.5 Hz); 2.05 (m, 2H); 1.58 (m, 4H); 1.44 (s, 9H); 1.32 (m, 6H), FABMS: m/z, 391(M+Li), 335. HRMS: m/z, $C_{15}H_{29}IO_3Li$, calc: 391.1322, found: 391.1353 (M+Li).

EXAMPLE 24 t-BUTYL-5-(1-IODO-HEXANE-6-OXA)PENTANOATE (38). The title compound 38 was prepared from 34 in a manner similar to the preparation of compound 36 in Example 22. Yield 77%. $^1$H NMR ($CDCl_3$) δ: 3.39 (m, 4H); 3.19 (t, 2H, J=6.9 Hz); 2.24 (t, 2H); 1.85 (m, 2H); 1.6 (m, 6H); 1.49 (s, 9H); 1.39 (m, 4H). FABMS: m/z 391 (M+Li); 335 and 211. HRMS: m/z, $C_{15}H_{29}IO_3Li$, calc: 391.1322, found: 391.1374 (M+Li).

EXAMPLE 25 t-BUTYL-2-(1-IODO-NONANE-9-OXA)ACETATE (39). The title compound 39 was prepared from 35 in a manner similar to the preparation of 36 in Example 22. Yield 69%. $^1$H NMR ($CDCl_3$) δ: 3.95 (s, 2H); 3.5 (t, 2H); 3.19 (t, 2H); 1.8 (m, 2H); 1.6 (m, 2H); 1.48 (s, 9H); 1.3 (m, 10H). FABMS: m/z, 391 (M+Li); 335, 329, 283 and 253.

EXAMPLE 26

9-(1-AZIDO-ETHANE-2-OXA)NONANOATE (40). A solution of 36 (0.45 g, 1.2 mmol) and iodotrimethylsilane (0.25 ml) in carbontetrachloride (3 mol) was stirred at room temperature for 1.5 h. The solution was concentrated under reduced pressure, 0.5N HCl (5 ml) and dichloromethane (15 ml) were added. The organic phase was washed with water (3×10 ml), dried ($Na_2SO_4$), concentrated and the residue was dried in vacuo to give 0.36 g. This product was dissolved in DMF (5 ml), sodium azide (0.24 g, 3.7 mmol) and 18-Crown-6 (0.025, 0,095 mmol) were added and the mixture was stirred at room temperature for 6 h. The solution was concentrated, 0.5N HCl (5 ml) was added and the mixture was extracted with ethylacetate (2×10 ml). The organic phase was washed with water (2×15 ml), dried ($Na_2SO_4$), concentrated under reduced pressure, and the residue was purified by flash chromatography (silica gel) using 20% EtOAc in hexane to give the title compound 40 (0.19 g, 64%) as a colorless liquid. $^1$H NMR ($CDCl_3$) δ: 3.6 (t, 2H); 3.47 (t, 2H); 3.38 (t, 2H); 2.35 (t, 2H, J=7.5 Hz); 1.61 (m, 4H); 1.32 (m, 8H); $^{13}$C NMR ($CDCl_3$) δ: 24.60, 25.86, 28.91, 29.09, 29.13, 29.53, 34.02, 50.72, 69.44, 71.39, 180.09. FABMS: m/z=261 (M+$NH_4$); 244 (M+H). HRMS: m/z=$C_{11}H_{21}N_3O_3Li$, calc: 250.1743, found: 250.1731 (M+Li).

EXAMPLE 27

8-(1-AZIDO-PROPANE-3-OXA)OCTANOIC ACID (41). The title compound 41 was prepared in a similar manner as compound 40 in Example 26 except that reactant compound 37 was substituted for an equivalent amount of 36. Yield 65%. $^1$H NMR ($CDCl_3$) δ: 3.48 (t, 2H, J=6.0 Hz); 3.41 (m, 4H); 2.35 (t, 2H, J=7.5 Hz); 1.84 (m, 2H); 1.6 (m, 4H); 1.34 (m, 6H). $^{13}$C NMR ($CDCl_3$) δ: 24.42, 25.76, 28.59, 29.05, 29.37, 33.81, 33.86, 48.36, 67.11, 70.92, 179.88. FABMS: m/z=261 (M+$NH_4^+$); 244 (M+H) and 216. HRMS: m/z=$C_{11}H_{21}N_3O_3Li$, calc: 250.1743, found: 250.1702 (M+Li).

EXAMPLE 28

5-(1-AZIDO-HEXANE-6-OXA)PENTANOIC ACID (42). The title compound 42 was prepared in a similar manner as compound 40 in Example 26 except that reactant compound 38 was substituted for an equivalent amount of 36. Yield 73%. $^1$H NMR ($CDCl_3$) δ: 3.4 (m, 4H), 3.29 (t, 2H, J=6.9 Hz); 2.4 (t, 2H, J=7.2 Hz); 1.65 (m, 8H); 1.39 (m, 4H). FABMS: m/z: 261 (M+$NH_4^+$); 244 (M+H) and 216. HRMS: m/z=$C_{11}H_{21}N_3O_3Li$, calc: 250.1743, found: 250.1779 (M+Li).

EXAMPLE 29

2-(1-AZIDO-NONANE-9-OXA)ACETIC ACID (43). The title compound 43 was prepared in a similar manner as compound 40 in Example 26 except that reactant compound 39 was substituted for an equivalent amount of 36- Yield 50%. $^1$H NMR ($CDCl_3$) δ: 4.09 (s, 2H, $OCH_2$); 3.58 (t, 2H, J=6.6 Hz); 3.26 (t, 2H, J=7.2 Hz); 1.61 (m, 4H); 1.32 (m, 10H). FABMS: m/z=250 (M+Li) and 228. HRMS: m/z=$C_{11}H_{21}N_3O_3Li$, calc: 250.1743, found: 250.1741 (M+Li).

EXAMPLE 30

12-(TETRAZOLYL)DODECANOIC ACID (46). A suspension of NaH (0.045 g, 80% suspension in oil) in DMF (1 ml) was added to a solution of tetrazole 44 (0.095 g, 1.35 mmmol) in DMF (1 ml). After stirring the reactants for 15 min, a solution of 12-iodo-dodecanoic acid 45 (0.2 g, 0.6 mmol) was added. The resulting mixture was stirred at room temperature for 1 h and at 55° C. for 1.5 h and then concentrated in vacuo. The residue was treated with 1N HCl(5 ml) and extracted with EtOAc (2×10 ml). The organic layer was washed with water, dried ($Na_2SO_4$), concentrated under reduced pressure and the residue was crystallized from EtOAc/Hexane to give the title compound 46 (0,095 g, 26%) as a 1:3 mixture of N-3 and N-1 isomers, respectively. This mixture was tested directly as a substrate for NMT. $^1$H NMR ($CDCl_3$) δ: 8.59 and 8.5 (2s, 1H); 4.65 and 4.43 (2t, 2H, J=7.2 Hz); 2.35 (t, 2H, J=7.5 Hz); 1.95 (m, 2H); 1.63 (m, 2H); 1.26 (m, 14H). FABMS: m/z 269 (M+H); 251 and 241. HRMS: m/z=$C_{13}H_{24}N_4O_2Li$, calc: 275.2059, found: 275.2004 (M+Li).

EXAMPLE 31

12-[1,2,4]TRIAZOLYCDODECANOIC ACID (48). To a suspension of sodium hydride (0.05 g, of 80% suspension in oil) in DMF cooled to 0° C., was added dropwise a solution of 1,2,4-triazole 47 (0.095 g, 1.38 mmol) in DMF (1.5 ml). The reaction mixture was stirred at 0° C. for 30 min., a solution of 12-iodododecanoic acid 45 (0.2 g, 0.6 mmol) and 18-crown-6 (0.01 g, 0.038 mmol) in DMF (1 ml), was added, and stirred at room temperature for 1 h and at 60° C. for 1.5 h. DMF was distilled under reduced pressure, the residue was dissolved in water (5 ml), acidified with 1N HCl to pH6 and extracted with ethyl acetate ($2 \times 15$ ml). The organic phase was washed with water ($2 \times 10$ ml), dried ($Na_2SO_4$) and concentrated under reduced pressure. The residue was purified by crystallization from ethyl acetate hexane (1:1) to give 48 (0.055 g, 34%) as a white powder. $^1H$ NMR ($CDCl_3$) δ: 8.10 (s, 1H), 7.96 (s, 1H), 4.17 (t, 2H, J=7.2 Hz), 2.35 (t, 2H, J=7.5 Hz); 1.88 (m, 2H), 1.63 (m, 2H), 1.26 (m, 14H). FABMS: m/z=268 (M+H).

EXAMPLE 32

12-(N-2-[1,2,3]TRIAZOLYL)DODECANOIC ACID (50). To a suspension of sodium hydride (0.13 g, ef 80% suspension in oil) in DMF (4 ml) cooled to 0° C., was added dropwise a solution of 1,2,3-triazole 49 (0.28 g, 0. 004 mmol) in DMF (1 ml). After 0.5 h, 18-crown-6 (0.025 g, 0.095 mmol) and 12-iodododecanoic acid 45 (0.5 g, 0.0016 mol) were added and the mixture was stirred for 1 h at room temperature and 1.5 h at 60° C. under nitrogen atmosphere. The reaction mixture was concentrated under vacuum, the residue was dissolved in water (10 ml), acidified with cold 1N HCl and the resulting mixture was extracted with ethyl acetate ($3 \times 15$ ml). The organic phase was washed with water ($2 \times 10$ ml), dried ($Na_2SO_4$), concentrated under reduced pressure and the residue was crystallized from ethyl acetate to afford the title compound 50 (0.12 g, 28%) as a white crystalline substance. m.p. 79°–80° C.; $^1H$ NMR ($CDCl_3$) δ: 7.59 (s, 2H), 4.44 (t, 2H, J=7.2 Hz); 2.35 (t, 2H, J=7.2 Hz), 1.95 (m, 2H); 1.63 (m, 2H), 1.26 (m, 14H). FABMS: m/z=274 (M+Li). HRMS: m/z=$C_{14}H_{25}N_3O_2Li$, calc: 274.2107, found: 274.2105.

EXAMPLE 33

A. Representative compounds prepared in the foregoing illustrative specific examples were analyzed in a conventional in vitro yeast N-myristoyltransferase (NMT) assay as published by Heuckeroth et al., *Proc. Nat'l Acad. Sci. USA* 85, 8795–8799 (1988). In this assay, the test compounds were first converted to their respective fatty acyl CoA derivatives and then tested as substrates for the yeast NMT.

The assay conditions [essentially the same as those reported by Towler and Glaser, *Proc. Natl. Acad. Sci. USA* 83, 2812–2816 (1986)] were as follows:

1. Ligase reaction: 3.3 μmoles fatty acid, 5 mM ATP and 1 mM CoA were incubated with 15–150 milliunits of CoA ligase (1 unit/ml in 50 mM HEPES, pH 7.3) in a buffer composed of 10 mM TRIS-HCl, pH 7.4, 1 mM dithiothreitol, 5 mM $MgCl_2$ and 0.1 mM EGTA, in a total volume of 50 μl for 25 minutes at 30° C.

2. NMT assay: 50 μl of the CoA ligase mixture was added to a 50 μl solution of 90 μM peptide (GSAA-SARR-$NH_2$) in a buffer composed of 10 mM TRIS-HCl, pH 7.4, 1 mM dithiothreitol, 0.01 mM EGTA and aprotinin (10 μg/ml). 0.4 Unit of yeast N-myristoyltransferase was then added and the reaction mixture was incubated at 30° C. for 10 minutes. The peptide was radiolabeled with tritiated alanine in position 3. The reaction was quenched with 120 μl of TCA-MeOH and 75 μl was injected on a reverse phase C18 HPLC column and eluted with a linear gradient of 0–100% acetonitrile over 100 minutes (both water and acetonitrile containing 0.1% trifluoroacetic acid). Radioactivity was assessed with an on line radiomatic detector corrected for quenching.

The amount of radioactivity was determined for each azido-substituted fatty acyl peptide product and then was normalized to the amount of myristoyl peptide produced in an assay run in parallel.

The activity of each fatty acid analog was thus expressed as a percentage of the activity exhibited by unsubstituted myristate (control) and recorded in the following Table 1.

TABLE 1

Substrate Activity of Azido-Substituted Fatty Acid Analogs

| Synthesis Example Test Compound | Myristate Analog Test Compound | Activity (% of Myristate) |
|---|---|---|
| Example 1 | $N_3(CH_2)_{11}COOH$ (1) | 142 |
| Example 2 | $N_3(CH_2)_{10}COOH$ (2) | 100 |
| Example 3 | $N_3(CH_2)_8COOH$ (3) | 55 |
| Example 26 | $N_3(CH_2)_2$—O—$(CH_2)_8COOH$ (40) | 28 |
| Example 27 | $N_3(CH_2)_3$—O—$(CH_2)_7COOH$ (41) | 42 |
| Example 28 | $N_3(CH_2)_6$—O—$(CH_2)_4COOH$ (42) | 62 |
| Example 29 | $N_3(CH_2)_9$—O—$CH_2COOH$ (43) | 11 |
| Example 10 | $N_3(CH_2)_6$—S—$(CH_2)_4COOH$ (13) | 103 |
| Example 13 | $N_3(CH_2)_9$—S—$CH_2COOH$ (19) | 17 |
| Example 23 | $N_3(CH_2)_8$—S—$(CH_2)_2COOH$ (23) | 37 |
| Example 30 | Tetrazolyl-$(CH_2)_{11}COOH$ (46) | 46 |
| Example 31 | 1,2,4-Triazoyl-$(CH_2)_{11}COOH$ (48) | 23 |
| Example 32 | 1,2,3-Triazoyl-$(CH_2)_{11}$—COOH (50) | 99 |

B. Representative compounds prepared in the foregoing illustrative specific examples were also tested in vitro for the assessment of anti-viral (HIV) activity as follows:

ASSAY INFORMATION

The HIV inhibition assay method of acutely infected cells is an automated tetrazolium based colorimetric assay adatped from that reported by Pauwles et al., *J. Virol. Methods*, 20, 309–321 (1988). Assays were performed in 96-well tissue culture plates. CEM cells were grown in RPMI-1640 medium (Gibco) supplemented with 10% fetal calf serum and were then treated with polybrene (2 μg/ml). An 80 μl volume of medium containing $1 \times 10^4$ cells was dispensed into each well of the tissue culture plate. To each well was added a 100 μl volume of test compound dissolved in tissue culture medium (or medium without test compound as a control) to achieve the desired final concentration and the cells were incubated at 37° C. for 1 hour. A frozen culture of HIV-1 was diluted in culture medium to a concentration of $5 \times 10^4$ $TCID_{50}$ per ml ($TCID_{50}$=the dose of virus that infects 50% of cells in tissue culture), and a 20 μl volume of the virus sample (containing 1000 $TCID_{50}$ of virus) was added to wells containing test compound and to wells containing only medium (infected control cells). This results in a multiplicity of infection of 0.1 (MOI=# of infectious virus particles/# of cells in culture). Several wells received culture medium without virus (uninfected control cells). Likewise, the intrinsic toxicity of the test compound was determined by adding medium without virus to several wells containing test compound. In summary, the tissue culture plates contained the following tests (in triplicate):

|   | cells | drug | virus |   |
|---|---|---|---|---|
| 1. | + | − | − | uninfected cell control |
| 2. | + | + | − | uninfected drug control |
| 3. | + | − | + | infected cell control |
| 4. | + | + | + | test case |

In tests 2 and 4 the final concentrations of test compounds were 1, 10, 100 and 500 µg/ml. Azidothymidine (AZT) was tested as a positive drug control, and dodecanoic acid was tested as a negative fatty acid control. Test compounds were dissolved in DMSO and diluted into tissue culture medium so that the final DMSO concentration did not exceed 1.5% in any case. Under these conditions, DMSO had no significant effect on results as determined in controls.

Following the addition of virus, cells were incubated at 37° C. in a humidified, 5% $CO_2$ atmosphere for 7 days. Additional aliquots of test compounds were added on days 2 and 5. On day 7 post-infection, the cells in each well were resuspended and a 100 µl sample of each cell suspension was removed for assay. A 20 µl volume of a 5 mg/ml solution of 3-(4,5-dimethylthiazol-2-yl)-2,5-diphenyltetrazolium bromide (MTT) was added to each 100 µl cell suspension, and the cells were incubated for 4 hours at 37° C. in a 5% $CO_2$ environment. During this incubation, MTT is metabolically reduced by living cells resulting in the production in the cell of a colored formazan product. To each sample was added 100 µl of 10% sodium dodecylsulfate in 0.01 N HCl to lyse the cells and samples were incubated overnight. The absorbance of each sample was determined at 590 nm using a Molecular Devices microplate reader. The % reduction of the virus induced cytopathic effect (CPE) by the test compounds was determined using the formula shown at the bottom of Table 2, hereinafter.

The results of the antiviral testing are set forth in Table 2, as percent reduction in cytopathic effect (CPE). The inhibitory dose that inhibits 50% of the cytopathic effect is shown as $ID_{50}$ (µg/ml).

TABLE 2

Antiviral Evaluation of Myristate Analogs Percent Reduction of $CPE^a$

| Compound | Concentration µ | | | $ID_{50}$ (µg/ml) |
|---|---|---|---|---|
|   | 100 | 10 | 1 |   |
| 13-Oxamyristate | T | $43.5^c$ | 66.4 | 0.3 Positive control |
| Decanoic acid $(C_{10})^b$ | T | 11.3 | 7.7 | — Negative control |
| 12-Azidododecanoic acid (1) | T | $38.2^c$ | 81.7 | 0.3 |
| 11-Azidoundecanoic acid (2) | T | $34.6^c$ | 16.3 | — |
| 12-Azido-9-oxa-DDA (41) | — | 66 | 14 | 5 |
| 12-Azido-3-oxa-DDA (43) | — | — | — | Inactive |
| 12-Azido-6-oxa-DDA (42) | — | 20 | 4 | Inactive |
| 12-azido-3-thia-DDA (19) | T | 54 | 1 | 9.2 |
| 12-azido-4-thia-DDA (23) | T | 0 | 0 | Inactive |
| 12-azido-6-thia-DDA (13) | T | 14 | 0 | Inactive |
| 12-tetrazoyl-DDA (46) | — | 65 | 12 | 5.9 |
| 12-(1,2,4-triazoyl)-DDA (48) | T | 66 | 24 | 4.2 |
| 12-(1,2,3-triazoyl)-DDA (50) | T | 30.8 | 19.5 | — |

DDA = Dodecanoic Acid

| Compound | 0.5 µ/ml | 0.1 µg/ml | 0.01 µg/ml | 0.001 µg/ml | $ID_{50}$ (µg/ml) |
|---|---|---|---|---|---|
| AZT | 87.8 | 100.8 | 84.8 | 58.2 | <0.001 |

$^a$The percent reduction of viral CPE was calculated by the formula:

$$\frac{\left(\begin{array}{c}\text{Absorbance of drug-treated,} \\ \text{infected sample}\end{array}\right) - \left(\begin{array}{c}\text{Absorbance of} \\ \text{virus control}\end{array}\right)}{\left(\begin{array}{c}\text{Absorbance of} \\ \text{cell control}\end{array}\right) - \left(\begin{array}{c}\text{Absorbance of} \\ \text{virus control}\end{array}\right)} \times 100.$$

$^b$Solubitlity problem; precipitate at highest test concentration.
$^c$Value may be arificially low because of partial toxicity at this test concentration.

The biologically active fatty acid analogs described herein can be used for administration to a mammalian host or host cells infected with retroviruses such as HIV and the like by conventional means, preferably in formulations with pharmaceutically acceptable diluents and carriers. The amount of the active agent to be administered must be an effective amount, that is, an amount which is medically beneficial but does not present toxic effects which overweigh the advantages which accompany its use. It would be expected that the adult human dosage would normally range upward from about one milligram of the active compound. A suitable route of administration is orally in the form of capsules, tablets, syrups, elixirs and the like, although parenteral administration also can be used. Appropriate formulations of the active compound in pharmaceutically acceptable diluents and carriers in therapeutic dosage form can be prepared by reference to general texts in the field such as, for example, Remington's pharmaceutical sciences, Ed. Arthur Osol, 16th ed., 1980, Mack Publishing Co., Easton, Pa.

Various other examples will be apparent to the person skilled in the art after reading the present disclosure without departing from the spirit and scope of the invention. All such other examples are included within the scope of the appended claims.

What is claimed is:

1. A composition of matter having a chemical structure as follows:

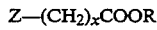

Z—$(CH_2)_x$COOR wherein
Z=azido, tetrazolyl or triazolyl,
R=H or $C_1$–$C_8$ alkyl,
X=7–11,
wherein an oxygen or sulfur is positioned between said two $CH_2$ groups from carbon position 2 to within 1 carbon or Z and wherein said tetrazolyl and said triazolyl are attached to said $(CH_2)_x$COOR at a primary nitrogen and wherein said tetrazolyl is a mixture of N-1 and N-3 isomers and said triazolyl is an N-1 isomer.

2. The compound of claim 1 in which Z is azido, R is H and a methylene group is replaced with oxygen.

3. The compound of claim 2 in which x is 6 and in which the methylene group in carbon position 6 is replaced with oxygen.

4. The compound of claim 2 in which x is 3 and in which the methylene group in carbon position 9 is replaced with oxygen.

5. The compound of claim 1 in which Z is azido, R is H and a methylene group is replaced with sulfur.

6. The compound of claim 5 in which x is 6 and in which the methylene group in carbon position 6 is replaced with sulfur.

7. A method of inhibiting virus in vitro in host cells infected with said virus comprising treating said host cells with a virally inhibitory effective amount of a fatty acid analog composition of matter of the following chemical structure:

Z—(CH$_2$)$_x$COOR wherein
Z = azido, tetrazolyl or triazolyl,
R = H or C$_1$–C$_8$ aklyl,
X = 8–12 and
wherein said tetrazolyl and said triazolyl are attached to said (CH$_2$)$_x$COOR at a primary nitrogen and wherein said tetrazolyl is a mixture of N-1 and N-3 isomers and said triazolyl is an N-1 isomer.

8. The method of claim 7 in which a methylene group from carbon position 3 to within 2 carbons of Z is replaced by oxygen or sulfur.

9. The method of claim 7 is which the virus is HIV.

10. The method of claim 9 in which the fatty acid analog is 12-azidododecanoic acid.

11. The method of inhibiting HIV virus in vitro in host cells infected with said virus comprising treating said host cells with a virally inhibitory effective amount f 2-(1-azido-nonane-9-thia)-acetic acid.

12. The method of inhibiting HIV virus in vitro in host cells infected with said virus comprising treating said host cells with a virally inhibitory effective amount of 8-(1-azido-propane-3-oxa)-octanoic acid.

13. The method of claim 9 in which the fatty acid analog is 12-(tetrazolyl)-dodecanoic acid.

14. The method of claim 9 in which the fatty acid analog is 12-([1,2,4-]-triazolyl)-dodecanoic acid.

15. The method of claim 9 in which the fatty acid analog is 12-([1,2,3]-triazolyl)-dodecanoic acid.

* * * * *

UNITED STATES PATENT AND TRADEMARK OFFICE
CERTIFICATE OF CORRECTION

PATENT NO. : 5,338,858

DATED : August 16, 1994

INVENTOR(S) : B. Devadas, J. I. Gordon and S. P. Adams

It is certified that error appears in the above-indentified patent and that said Letters Patent is hereby corrected as shown below:

Column 16, line 66, "said two" should read --two said--.

Column 17, line 5, "6" should read --10--.

Column 17, line 8, "3" should read --10--.

Column 17, line 13, "6" should read --10--.

Signed and Sealed this

Thirteenth Day of June, 1995

Attest:

BRUCE LEHMAN

*Attesting Officer*   *Commissioner of Patents and Trademarks*